United States Patent [19]

Kirianoff

[11] 4,024,856

[45] May 24, 1977

[54] METHOD AND APPARATUS FOR MEASURING THE VOLUME OF ASYMMETRICAL BREASTS

[76] Inventor: Timofey Gregory Kirianoff, 2080 Century Park East, Los Angeles, Calif. 90067

[22] Filed: Oct. 30, 1975

[21] Appl. No.: 627,126

[52] U.S. Cl. .................................. 128/2 S; 3/36; 33/174 D
[51] Int. Cl.² ......................................... A61B 5/10
[58] Field of Search ................... 128/2 S, 462, 505; 33/2 R, 174 D; 3/36

[56] References Cited

UNITED STATES PATENTS

| | | | |
|---|---|---|---|
| 2,553,825 | 5/1951 | Langs | 128/505 |
| 2,597,924 | 5/1952 | Davenport et al. | 128/462 |
| 2,697,229 | 12/1954 | Krueger | 128/462 |
| 2,725,633 | 12/1955 | Graf | 33/2 R |
| 2,741,769 | 4/1956 | White | 128/462 |
| 2,826,202 | 3/1958 | Star | 128/462 |
| 2,946,125 | 7/1960 | Gittelson | 33/2 R |

Primary Examiner—Kyle L. Howell
Attorney, Agent, or Firm—J. B. McGuire

[57] ABSTRACT

A template of predetermined size and shape for receiving a human breast and having a seal about the periphery thereof for contact with the skin of a patient. A pair of conduits extend through the template; one conduit may be attached to a syringe or other device for injection of a measured volume of fluid into the cup. The second conduit allows air to be exhausted from within the cup as the fluid is injected and allows the person injecting the fluid to ascertain when the cup is full.

9 Claims, 4 Drawing Figures

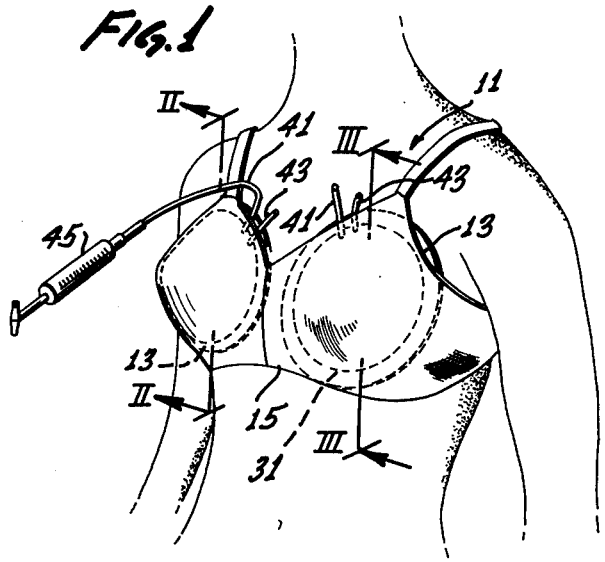
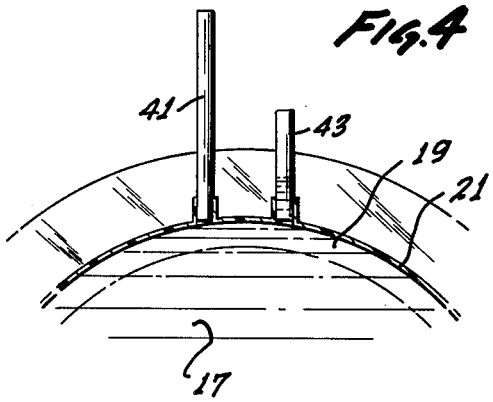
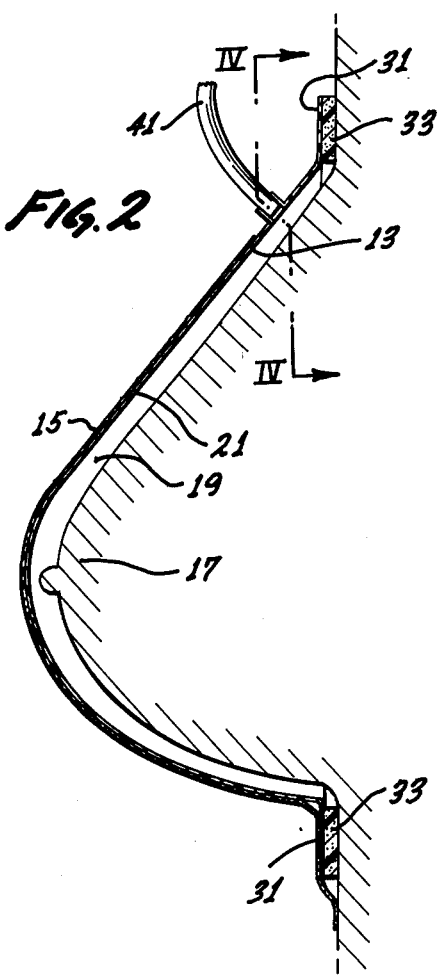
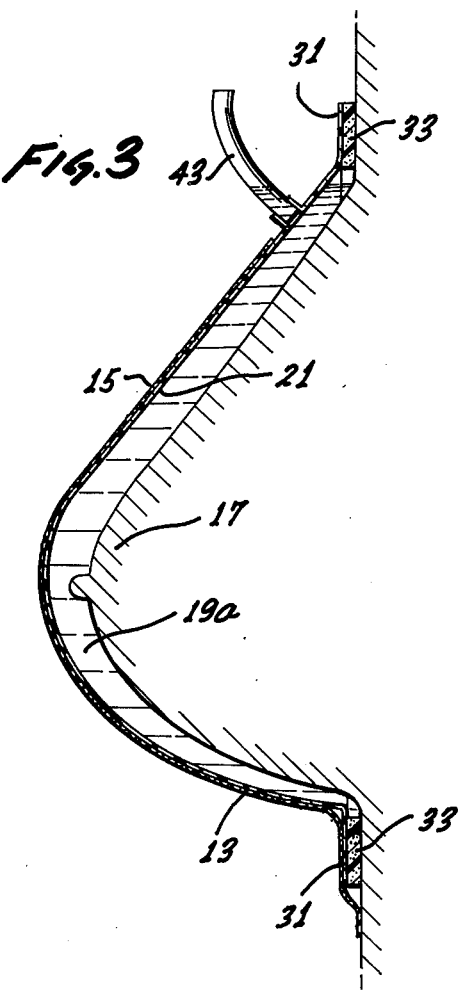

METHOD AND APPARATUS FOR MEASURING THE VOLUME OF ASYMMETRICAL BREASTS

BACKGROUND OF THE INVENTION

Many women today desire to have their breasts enlarged and/or uplifted in order to improve their appearance. Such an operation, medically referred to as "augmentation mammaplasty," has become fairly common, particularly the insertion of gel implants into the breasts.

In order to ensure the success of such an operation, it is desirable that the breasts, after the insertion of the implants, are of about equal size. Unfortunately, it is usually the case that the woman's breasts are of unequal size prior to the operation. However, it has been found desirable that the breasts be of about equal size when the operation has been accomplished.

Accordingly, it has been necessary to find some method and apparatus for not only measuring the size of each breast accurately, but for determining the difference between the size of the breast so that the gel implants can be formed accordingly.

In the past, rather inexact methods for obtaining these measurements have been utilized. Such methods have involved tape measures, etc., but the results have proven to be substantially unsatisfactory.

SUMMARY OF THE INVENTION

The present invention relate to a very simple and fast method of measuring the size of each breast, relative to a predetermined volume, and for determining the difference in size between a woman's right breast and left breast.

Basically, the method comprises the installation of a preformed template over a breast and the insertion of a fluid into the template about the breast while measuring the volume of fluid injected. Preferably, the template is releasably sealed to the skin of the patient about the breast in order to prevent inadvertent leakage from within the cup. Also, structure may be provided for allowing air within the cup to be exhausted. Preferably, the exhaust system can be transparent so that the doctor is able to ascertain when the cup is full, without allowing the fluid to overflow.

Upon reading the following description, taken together with the drawing, those skilled in the art will quickly realize that a variety of such devices may be provided, both simple and complex in form, many of which may not even resemble the described and illustrated structure but which, nevertheless, employ the invention as set forth in the claims.

BRIEF DESCRIPTION OF THE DRAWINGS

FIG. 1 comprises an isometric illustration of the manner in which a device formed in accordance with the present invention may be employed;

FIG. 2 comprises a sectional illustration of the device illustrated in FIG. 1, as seen along the line II-13 II, and particularly illustrating the fluid injection conduit;

FIG. 3 comprises a view similar to FIG. 2, taken along the line III—III of FIG. 1, illustrating a cup filled with fluid and particularly showing the exhaust conduit; and FIG. 4 comprises a partial sectional view of a device as shown along the line IV—IV of FIG. 2.

DETAILED DESCRIPTION

As shown in FIG. 1, a female patient whose breasts are to be measured is depicted at 11. As shown, a template 13 may be located over each of her breasts and, if desired, may be held in place by means retaining such as a brassiere 15.

Referring to FIGS. 2–4, it can be seen that each template has a cup portion or member 21 suitably formed so as to receive the entire breast 17. The remaining volumes 19 and 19a formed between the extremities of the breasts and the cup portions or member 21 of the templates 13 are shown as unequal (as in the average case) by comparing FIGS. 2 and 3.

About the periphery of each template, a flange-like portion 31 may be provided, to which a sealing element 33 may be fixedly attached. The sealing element may be of any suitable material, such as rubber or plastic, and should be locatable tightly against the skin of the patient about the entire breast. Preferable, the seal 33 prevents communication between the volume 19 (or 19a) inside the cup with the exterior of the template, except through a pair of conduits 41 and 43 in each template.

The conduit 41 may, if desired, be slightly longer than the conduit 43. This will allow the conduit 41 to be quickly and easily attached to a suitable injection apparatus, such as a syringe 45, which may contain a suitable fluid such as water. As the syringe or other injection device is actuated in the usual manner, a measured quantity of water may thus be injected into the volume 19 or 19a in the cup 21 to which it is connected. As stated previously, comparison of FIGS. 2 and 3 quickly reveals that the volume 19 at the right breast is somewhat smaller than the volume 19a at the left breast. Consequently, a greater quantity of fluid will be injected into the colume 19a than into the volume 19. Thus, each breast can be compared, in size, to a standard size and to the other breast.

As fluid is injected, air within the volume will exhaust through the conduit 43 to the atmosphere. If the conduit 43 is formed of a transparent material, as shown in FIG. 3 the water level will be visible to the doctor so he knows instantly when the cup is full and injection should stop.

It will be realized by those skilled in the art that it is not necessary to provide two templates to accomplish this task. Since each template is preformed, it could be utilized, first with one breast and then with the other. However, if the templates are substantially identical, the procedure will take less time since the doctor need not empty and remove the template and then install it over the other breast before measuring it.

Since the volume of the cup portion within each template is known at the time the template is formed, the exact size or mass of the breast can be easily determined by subtracting, from the volume of the cup, the volume of the fluid injected. In other words, each breast can be measured individually and, further, the difference in size of the breasts can be calculated utilizing this structure in the described process.

As stated previously, those skilled in the art will quickly become aware of a wide variety of structures which could be employed to accomplish the method, within the scope of the invention both as to the apparatus and method.

I claim:

1. Apparatus for measuring the volume of a breast comprising
   a cup-like template suitably sized to contain and encompass a breast to be measured and having
      an interior wall locatable in proximity to a breast to be measured,
      sealing means about the periphery thereof for contact with a patient's skin in the area about the breast to be measured,
      a first connector means in said template for passage of a liquid into the volume formed between said interior wall and the breast to be measured when the template is sealed against the patient's skin by said sealing means, and
      a second connector means in said template for passage of fluid out of the volume between said interior wall and the patient's breast as liquid is injected into the volume,
   means for moving a liquid through said first connector, and
   means for measuring the volume of a liquid moved into the volume between said interior wall and a patient's breast through said first connector.

2. The apparatus of claim 1 including
   means for retaining said template against the skin of a patient so that said sealing means is maintained in sealed relationship with the skin.

3. Apparatus for measuring the relative volumes of breasts comprising
   a template including
      a cup portion so sized as to receive a human breast therein,
      flange means extending about the periphery of said cup portion, and
      sealing means fixed to said flange means and so located thereon as to contact the skin of a patient about the breast when the breast is positioned in said cup portion,
   means for controlling the injection of a liquid into said cup portion from the exterior thereof, and
   means for measuring the volume of liquid injected into said cup portion.

4. The apparatus of claim 3 wherein
   said controlling means comprises
      a conduit for transfer of liquid into said cup portion form the exterior of said template, and
      means for exhausting air displaced by liquid entering said cup portion.

5. The apparatus of claim 4 wherein
   said exhausting means comprises a second conduit which is so located on said template as to prevent overflow of liquid entering said cup portion when the air has been totally exhausted therefrom.

6. The apparatus of claim 3 including
   means for exhausting a substantially equal volume of air from within said cup portion as liquid is injected thereinto by said controlling means.

7. Apparatus for determining the variation of size of a human female breast from a predetermined standard size comprising
   template means having
      a cup portion suitable for receiving and encompassing a human breast and having an internal volume of predetermined size and
      sealing means located about the entire periphery of said cup portion for contact with the skin about a breast positioned therein, and
   means for injecting a volume of liquid into said cup portion about a breast postioned therein and for measuring the volume of liquid thus injected.

8. The method of determining the variation of size of a human female breast from a predetermined standard size comprising the steps of
   inserting the breast to be measured into a cup shaped member of predetermined volume,
   sealing the periphery of the cup-shaped member to the skin about the breast therein,
   injecting a liquid into the cup-shaped member about the breast therein,
   stopping said injecting step when the air within the cup shaped member about the breast has been expelled therefrom, and
   determining the volume of liquid which has been injected into the cup-shaped member.

9. The method of claim 8 including
   measuring the asymmetry of the breasts of a human female by
   accomplishing the steps set forth in claim 8 for each breast and
   ascertaining the difference between the volumes of liquid injected into said cup-shaped member with each breast therein.

* * * * *